US006213958B1

(12) United States Patent
Winder

(10) Patent No.: US 6,213,958 B1
(45) Date of Patent: Apr. 10, 2001

(54) METHOD AND APPARATUS FOR THE ACOUSTIC EMISSION MONITORING DETECTION, LOCALIZATION, AND CLASSIFICATION OF METABOLIC BONE DISEASE

(76) Inventor: Alan A. Winder, 56 Patrick Rd., Westport, CT (US) 06880

( * ) Notice: Subject to any disclaimer, the term of this patent is extended or adjusted under 35 U.S.C. 154(b) by 0 days.

(21) Appl. No.: 09/167,868

(22) Filed: Oct. 7, 1998

Related U.S. Application Data

(60) Provisional application No. 60/025,487, filed on Aug. 29, 1996, and provisional application No. 60/061,359, filed on Oct. 8, 1997.

(51) Int. Cl.[7] .................................................. A61B 5/00
(52) U.S. Cl. ............................................ 600/586; 600/442
(58) Field of Search ..................................... 600/586, 587, 600/594, 595, 301, 442, 449

(56) References Cited

U.S. PATENT DOCUMENTS 5,259,384 * 11/1993 Kaufman et al. ..................... 600/442
5,400,795 * 3/1995 Murphy et al. ....................... 600/515
5,785,656 * 7/1998 Chiabrera et al. .................... 600/449

OTHER PUBLICATIONS

Application of correlation techniques for localization of acoustic emission sources, by I. Grabec, 1978, IPC Business Press Ltd., pp. 111–115.
Application of an intelligent signal processing to acoustic emission analysis, by Igor Grabec and Wolfgang Sachse, Mar. 1989, Acoustic Society of America.
Ultrasound as a Tool for Investigating Bone: Fundamental Principles and Perspectives for Use in Osteoporosis*, by J.G. Bloch, 1993, Expansion Scientifique Francaise.
Acoustic Emission Inspection, by Adrian A. Pollock, 1992, ASM Handbook, vol. 17, Nondestructive Evaluation and Quality Control, pp. 278–293.
Acoustic Emission—An Update, by Arthur E. Lord, Jr., 1981, Physical Acoustics, vol. XV, pp. 295–360.
Acoustic Emission Techniques in the Development of a Diagnostic Tool for Osteoporosis, by S. Hanagud and R.G. Clinton, 1975, Ultrasonic Symposium Proceedings (IEEE), pp. 41–45.
Acoustic Emission and Diagnosis of Osteoporosis, by S. Hanagud, G.T. Hannon and R. Clinton, 1974, Ultrasonic Symposium Proceedings (IEEE), pp. 77–81.
Acoustic Emission in Bone Substance, by S. Hanagud, R.G. Clinton and J.P. Lopez, 1973, Biomechanics Symposium Proceedings (ASME), pp. 79–81.

* cited by examiner

Primary Examiner—Cary O'Connor
Assistant Examiner—Pamela L. Wingood
(74) Attorney, Agent, or Firm—Kilpatrick Stockton LLP

(57) ABSTRACT

A non-invasive bone condition data acquisition system performs sensitive and reliable clinical data acquisition, localization and classification of bone disease, particularly osteoporosis. The bone condition data acquisition system measures a correlation between a wideband AE signature and a spatially localized bone microarchitecture, which is used to determine fracture risk. The bone condition data acquisition system includes processors and memory for analyzing AE signals from bone tissue to generate information-bearing attributes, for extracting a set of times-of-arrival and a feature vector from the attributes, for utilizing the set of times-of-arrival to derive the locations of the AE events, and for responding to the feature vector to classify the bone using a neural network and a nearest neighbor rule processor.

38 Claims, 4 Drawing Sheets

METHOD AND APPARATUS FOR THE ACOUSTIC EMISSION MONITORING DETECTION, LOCALIZATION, AND CLASSIFICATION OF METABOLIC BONE DISEASE

This application claims priority to U.S. Provisional Application No. 60/061,359 filed Oct. 8, 1997, entitled "Acoustic Emission Monitoring for the Detection, Localization, and Classification of Metabolic Bone Disease.

BACKGROUND INFORMATION

1. Technical Field

This disclosure relates to the determination of the condition of bone, and in particular to a system and method for monitoring acoustic emissions of bones for detecting, localizing and classifying the condition of such bones.

2. Description of the Related Art

Osteoporosis is a major public health problem which is projected to affect even larger numbers of people as the population continues to age and life spans have been extended. It has been estimated that over 1.5 million osteoporotic fractures occur annually in the United States. As new treatments for osteoporosis become available, one challenge is to improve the ability to identify those people with decreased bone quality and increased risk of osteoporotic fracture, so that effective interventions may be instituted.

Osteoporosis is a disorder currently characterized by a decrease in bone mass and a propensity to develop fractures. Osteoporosis tends to remain asymptomatic, and is often unrecognized until the development of the first fracture. The distal forearm, thoracic and lumbar vertebrae, and the proximal femur are the locations of the most common osteoporotic fractures. The occurrence of any one of these fractures may cause significant morbidity and alteration in lifestyle, including cost of care. A forearm fracture may leave an elderly woman unable to dress and care for herself. Vertebral fractures may be either asymptomatic or may lead to disabling back pain and nerve compression. The morbidity, mortality, and cost associated with hip fractures is substantial. Of those people able to walk at the time of the hip fracture, nearly half will not be able to ambulate without assistance following the fracture. Both the short term and long term costs of caring for hip fracture patients have a tremendous impact on health care expenditures. It has been estimated that the number of hip fracture rates per year in the United States is greater than 250,000, with the direct and indirect costs annually being in the range between $7 billion and $10 billion. Annual estimates for the year 2020, due to the growing size of the elderly population, are between $31 and $62 billion.

Although osteoporosis has been considered to be a disorder primarily affecting post-menopausal women, other large groups of the population are at increased risk for osteoporosis and osteoporotic fractures, including those people receiving steroid and immunosuppressive therapy, and elderly men. Many people who have osteoporosis are asymptomatic until the fracture. One of the major challenges of treatment of osteoporosis is the ability to identify people who are at increased risk of future fracture and to intervene with an effective therapy.

The availability of improved methods of measuring bone mineral density (BMD), such as dual photon absorptiometry (DPA) and dual energy X-ray absorptiometry (DEXA), has greatly improved the ability to identify people who are at increased risk of developing osteoporotic fractures. BMD is an indirect measure of bone strength. However, it has been recognized that a segment of the population will develop osteoporotic fractures despite a normal BMD. In addition, not all patients with decreased BMDs will develop osteoporotic fractures. Other factors, such bone microarchitecture, accumulation of microfractures, and skeletal aging itself are likely to contribute to bone strength and risk of fracture. Current studies have reported ROC curves with values of about 80%.

A non-invasive, safe, and reliable technique to determine bone quality would substantially improve the ability to detect people at risk for the development of fractures, and would be an invaluable technique to monitor response to therapy. Such a technique would need to be better than BMD measurements in the prediction of fracture risk if it is to substantially alter the ability to diagnose osteoporosis and to determine fracture risk.

A primary standard for predicting fracture risks is the accurate measurement of mechanical strength of bone. The goal to non-destructively measure bone strength in vivo has heretofore not been achieved. A scientific method of determining strength of complex structures has been successfully used in the field of non-destructive testing. This method requires the measurement of acoustic emission (AE) signals from stressed materials. Use of AE monitoring (AEM) in bone tissue has so far relied only on the very unsophisticated method of simply counting the number of AE events as a function of time. The approach of treating an AE event as a narrowband process, primarily to minimize measurement noise, and measuring the emission rate during application of stress, has heretofore not been successful when applied in biological systems.

The accompanying sudden, localized change of stress or strain in bone tissue produces wideband AE signals. These changes in stress and their corresponding acoustic emissions are uniquely related to the location and type of changes in bone mass, strength, and architecture, referred herein as bone quality. Generally, almost all bone fractures are preceded by subtle but distinct changes in an AE signature of the bone, and different fatigue modes influence the AE signature differently.

The biological AE signal field may thus be extremely rich with biological information which has not been successfully and effectively exploited for diagnosing osteoporotic conditions.

The term "acoustic emission" is used to describe stress waves emitted by rapid structural changes in material or a solid body. If a force or load applied to the structure causes an inhomogeneity to change in response to the local stress field, a local stress differential will be induced. The stress differential acts as the source of radiation for elastic waves to propagate throughout the structure. Transducers on the surface of the structure will detect these bursts of energy as AE signals, which are naturally wideband phenomena. This mechanism is valid for both non-biological and biological media.

Conventional AE data acquisition methods are essentially scaler measures which utilize narrowband transducers to measure the number of times the root-mean-square (rms) power exceeds a given threshold as a function of time, and is usually referred to as the "AE rate". If the character of the naturally wideband AE signal is preserved and a vector measure is obtained with spatial array processing, then knowledge about the source distribution may be derived from the set of AE signals recorded at multiple observation points, maintaining the relative times-of-arrival. The source of radiation for a given defect will be weighted by the characteristics of the incurred propagation paths and the measuring instrumentation. A complete description of the source distribution therefore requires a reasonably accurate, functional model of the structure architecture and calibration of the instrumentation.

Over the past twenty years, research teams have utilized scaler AE data acquisition and monitoring for a broad range of applications, including both non-biological and biological media. It is now well established that AEM may be effectively employed to: assess soil stability of dams; dikes, retaining walls, and lagoon embankments; and detect and monitor leaks from underground gasoline storage tanks and buried pipelines.

Acoustic emissions are also produced in materials, such as metal and plastic when they are subjected to stress such that they undergo deformation, fracture, or both. AE occurs after "yield", the end of the material's elastic state and the beginning of its plastic state. A strong correlation has been shown to exist between stress versus strain and stress versus AE.

Energy Release Processors (ERP) have been developed for locating flaws and discontinuities in complex piping systems and long runs of buried piping, with the ERP system providing an early warning of significant defect growth. AEM has also revealed the presence of significant cracks in welds of stainless steel steam lines in a thermal power plant. AE patterns have also been successfully measured for fiber-reinforced composites, and composite rocket motor cases. AEM has also been found effective in detecting and pin-pointing medium to high pressure leaks in gas distribution systems.

AEM technology has been investigated by several researchers in the 1970's as a diagnostic tool for osteoporosis. It has been shown that the acoustic emission rate from cattle femurs subjected to bending loads is greater for low density specimens as compared to femurs with normal density. These emissions were detected well before the actual bone failure. Recent studies have examined the acoustic emissions from cancellous bone under compression, which also demonstrated that the post-yield acoustic emission rates are significantly higher in both osteoporotic and osteoarthritic bone specimens as compared to normal bone specimens. Results of such studies show a relationship between AE counts versus the applied load and between AE rates versus the applied load.

To date, the major shortcomings of AEM experiments performed on bone tissue are that: (1) they were essentially narrowband measurements not matched to the informational bandwidth of the AE source distribution; (2) the information-bearing attributes of the emitted signals and the structural differences between them were not investigated; and (3) the transient signals normally-occurring in human tissue and in a clinical environment were not evaluated and processed for proper data normalization and signal-to-noise enhancement. The sensitive and reliable data acquisition of incipient bone defects should preserve the spatial and temporal characteristic features in a measurable database that define normal conditions and the features associated with degradation. These characteristic features are referred to as the information-bearing attributes of the AE signature, and are intimately related to the physics and quality of bone tissue.

Other studies have related ultrasonic wave propagation measurements to the structure and anisotropic mechanical properties of osteoporotic and osteopetrotic bone. Bone tissue is a dispersive, anisotropic medium. Acoustic propagation in bone undergoes both geometric and viscoelastic dispersion, with attenuation increasing almost linearly over the frequency range 1–15 kHz. Osteoporosis is characterized by increased porosity or decreased density, while osteopetrosis forms calcified cartilage in bone.

Previous studies of ultrasound have focused on the use of broadband ultrasound attenuation (BUA) for the determination of bone strength. BUA has been found to correlate significantly with BMD as measured by single X-ray absorptiometry; yet there was sufficient variability in the measurements to suggest that BUA provides at least some information about bone in addition to BMD. BUA of the os calcis has been shown to be a better discriminator of hip fracture than DEXA of the lumbar spine or hip. These preliminary observations suggest that ultrasound may provide additional information regarding bone microarchitecture and bone strength.

SUMMARY

A non-invasive bone condition data acquisition system is disclosed for sensitive and reliable clinical data acquisition, localization and classification of bone disease, particularly osteoporosis. The bone condition data acquisition system measures a correlation between a wideband AE signature and a spatially localized bone microarchitecture, which is used to determine bone quality and fracture risk.

The bone condition data acquisition system treats the biological AE signature as a true wideband process, as it naturally occurs during the physical generation process. The bone condition data acquisition system provides the spatial precision required to isolate the AE events in the region-of-interest (R-O-I) and permits the fine detail parameters of the AE signatures to be measured and tracked. The bone condition data acquisition system includes processors and memory for analyzing AE signals from stressed bone tissue to generate information-bearing attributes, for extracting a set of times-of-arrival and a feature vector from the attributes, for utilizing the set of times-of-arrival to derive the locations of the AE events, and for classifying bone quality by using the feature vector to drive a neural network and a nearest neighbor rule processor.

The system applies highly advanced processing methods that characterize and are sensitive to structural changes in bone architecture, as well as to the macro-mechanical properties of the bone. A lower data acquisition threshold is established to classify AE signals from bone, and the correlation of the AE signals with bone strength is ascertained. The information-bearing attributes of AE signals are based on a realistic model of the bone-soft-tissue-skin complex and signal identification analysis methods.

The system is used for in vivo testing and calibration using normal human volunteers. The system is applicable in the data acquisition, localization and classification of osteoporosis by determining the set of AE profiles in patients with demonstrated decreased bone strength as evidenced by history of osteoporotic fracture. The AE profile is used as a better predictor of decreased bone strength than is BMD testing by DEXA.

BRIEF DESCRIPTION OF THE DRAWINGS

The features of the disclosed bone condition data acquisition system and method will become more readily apparent and may be better understood by referring to the following detailed description of illustrative embodiments of the present invention, taken in conjunction with the accompanying drawings, in which.

DESCRIPTION OF THE PREFERRED EMBODIMENTS

Figure 1:
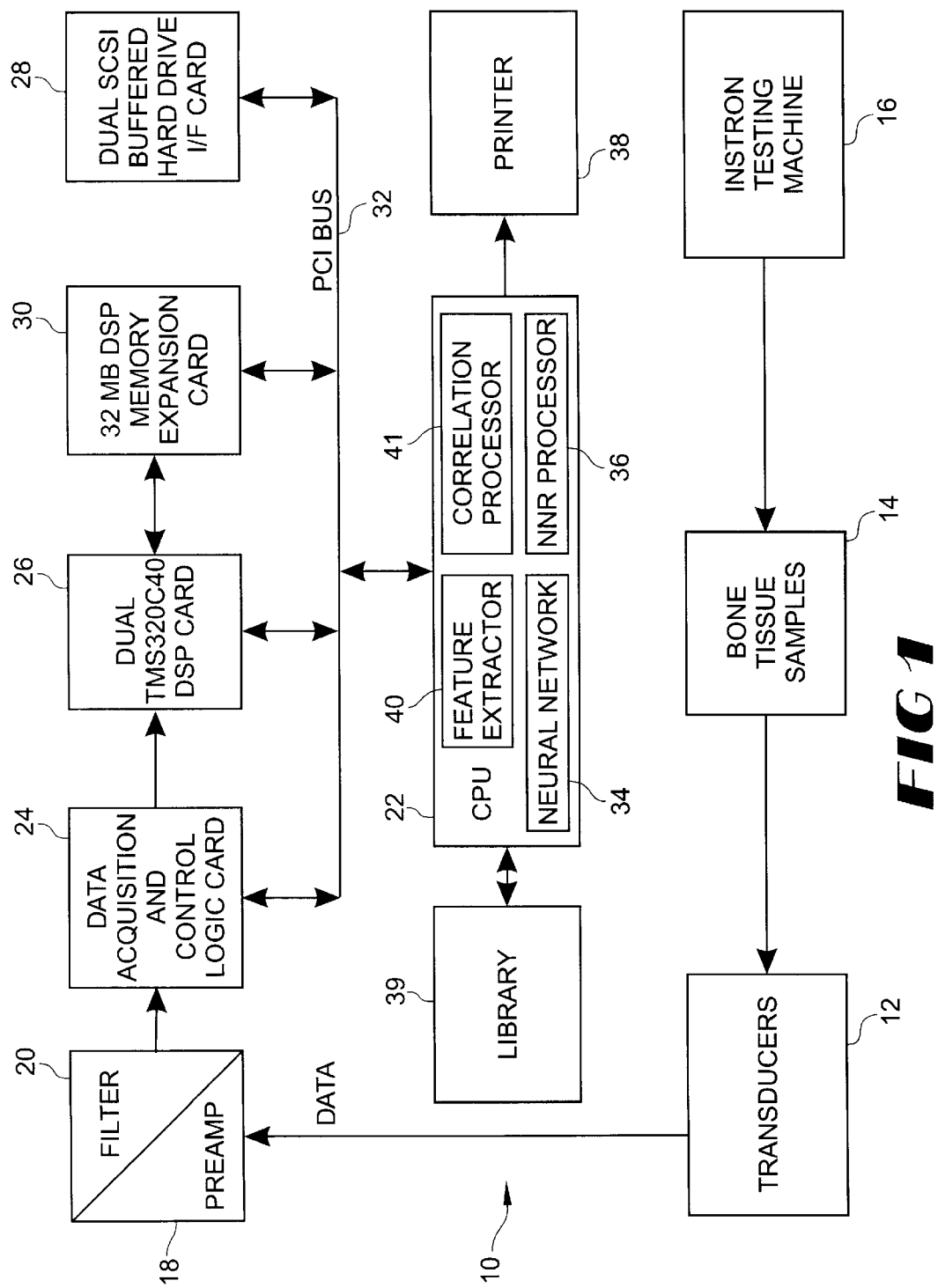
FIG. 1 is a block diagram of a bone condition data acquisition system of the present invention.

Referring now in specific detail to the drawings, with like reference numerals identifying similar or identical elements, as shown in FIG. 1, the present disclosure describes a system 10 and method using acoustic emission monitoring for the data acquisition, localization, and classification of metabolic bone disease.

For clarity of explanation, the illustrative embodiments of the disclosed bone condition data acquisition system 10 and method are presented as having individual functional blocks, which may include functional blocks labelled as "processor" and "processing unit". The functions represented by these blocks may be provided through the use of either shared or dedicated hardware, including, but not limited to, hardware capable of executing software. For example, the functions of the processor and processing unit presented herein may be provided by a shared processor or by a plurality of individual processors. Moreover, the use of the functional blocks with accompanying labels herein is not to be construed to refer exclusively to hardware capable of executing software. Illustrative embodiments may include digital signal processor (DSP) hardware, read-only memory (ROM) for storing software performing the operations discussed below, and random access memory (RAM) for storing DSP results. Very large scale integration (VLSI) hardware embodiments, as well as custom VLSI circuitry in combination with a general purpose DSP circuit, may also be provided. Any and all of these embodiments may be deemed to fall within the meaning of the labels for the functional blocks as used herein.

The transducers 16 may include an array of one to at most sixteen, but most likely six, piezoceramic sensors with stand-off gel pads to sample the AE field at the surface of the bone samples 14. In one embodiment, specific wideband acoustic emission sensor/preamplifier devices, such as those produced by Dunnegan Engineering Consultants Inc., provide a receiving response from 30 kHz to more than 3 MHz, and preferably from about 100 kHz to 1 MHz. Other sensors may also be used, such as piezoceramic transducers on the end of needle probe tips; a fiber optic laser interferometer, available from Epoch Engineering, Inc., for measuring a tissue sample's surface vibrations; and a class of highly crystalline and oriented thermoplastic polymers, such as polyethylene teraphthalate, etc. for producing a broadband frequency response, from 10 kHz to 5 MHz.

In the illustrative embodiment of FIG. 1, the system 10 is configured to provide multi-sensor/channel data acquisition, utilizing wideband sensors and spatial, temporal and Fourier processing to detect and characterize the AE signals. The transducers 12 are simultaneously monitored to derive the source stress differential history associated with a given AE event. A database of collected data is derived from various controlled stages of bone model degradation. Subtle changes expected in bone defects implies a low noise, high input dynamic range system.

The system 10 has a dynamic range of about 72 dB (i.e. 12 bits) for the received signal plus noise signature. Based upon AEM studies of bone tissue by the inventor and others, the AEM spectra is acquired over a frequency range from about 30 kHz to about 3.0 MHz, and preferably from about 100 kHz to about 1 MHz.

A major consideration are the cross-talk capacitances on the signal lines. Placing ground leads between signal lines greatly reduces capacitances between signals and replaces them with capacitances to ground. The entire array assembly of transducers 12 may be completely shielded with sheets of ground planes to reduce the effects of environmental electromagnetic noise.

The system 10 processes input data signals provided by a plurality of transducers 12 which respond to AE signals generated by bone tissue samples 14 under test by an INSTRON testing machine 16, which is a device capable of applying a broad range of carefully controlled loads to bone tissue under test for determining strain values. The input data signals are processed by a pre-amplifiers 18 and then filtered by filters 20. The filtered data signals are then processed by a processing unit which includes a central processing unit (CPU) 22 operating in conjunction with a data acquisition and control logic card 24, and a DSP card 26. The CPU 22 and other components of the system 10 may be controlled by an application program written, for example, in the C++ or visual basic programming language to implement the features and methods described herein.

The memory may be a hard drive 28 and/or RAM, and the optional RAM on the DSP card 26 may be used for faster memory access and processing. The hard drive 28 and cards 24, 26 communicate with the CPU 22 using a bus, such as an PCI bus operating the PCI protocol. The CPU 22 includes a neural network 34 and may also include a nearest neighbor rule (NNR) processor 36, as described in greater detail below. A library 39 of bone defects is accessed by the neural network 34 and/or NNR processor 36 to facilitate classification.

After processing the input data signals, the system 10 generates an output signal for hard copy by an output device such as a printer 38, or optionally a display, an audio system, or other types of output devices known in the art. The output device may output alpha-numeric text messages indicating the condition of the tested bone tissue samples, and/or may output a classification message indicating the degree to which the bone tissue samples under test are within or outside predetermine normal bone conditions, for example, a percentage compared to 100% normal may be generated and output.

In an illustrative embodiment, the data acquisition and control logic card 24 may be the 12 bit, 60 MHz Signatec DA60, the CPU 22 may be an "INTEL"-based "PENTIUM" microprocessor, and the DSP card 26 may be a quad TMS220C6201. The hard drive interface card 28 may feed two Seagate 18.2 GB fast SCSI hard drives to provide a total storage capacity of about 36.4 GB. Algorithmic processing will be used to identify true AE events, using the information-bearing attributes of the AE signals, to minimize the amount of storage required. System calibration and data acquisition thresholding will ensure a low false alarm rate.

The data acquisition and control logic card 24 formats the data to be in standard personal computer file formats, such as ASCII data formats, to allow the data to be replayed in the laboratory using modified system software and/or using commercial third-party analysis software, such as application programs known as S-PLUS and MAPLE. Real-time performance is achieved through the use of multiple COTS DSP boards for DSP card 26. The DSP card 26 is used to acquire the data, to pack and pass the data to the CPU 22 for storage via the hard disk card 28, and to simultaneously band-pass the data, low-pass filter and decimate the band-passed data, and to perform various processing operations such as data normalization, fast Fourier transform (FFT) analysis and parameter estimation.

The output of the transducers 12 are sent over, for example, coaxial cables to individual pre-amplifiers 18, which may be separate and independent low noise, wide-band programmable gain amplifiers, such as the AD 601 which is commonly used in medical ultrasound, to provide an input dynamic range of about 80 dB while minimizing noise and distortion. The pre-amplifiers 18 may be configured on a computer card or board which plugs into the system 10, which may be embodied as a personal computer or workstation, and which allows the user to change gain settings through software controls without degrading the frequency response as the gain is increased. The filters 20 may be anti-aliasing filters subsequent to the pre-amplifiers 18 to provide a very high rolloff rate of about −84 dB/octave. This can be achieved utilizing delay equalized elliptic filters, as provided by TTE Inc.

The output of the anti-aliasing filters 20 is sent to the data acquisition and control logic card(s) 24, which may include, for example, one 12-bit differential 30 MHz analog-to-digital converter (ADC) per sensor channel. A sixteen channel system will require a throughput rate of 1 Gbyte per second. Each channel of the ADCs may have its own sample and hold circuit to eliminate time skews and a programmable gain amplifier with sufficient gain to provide the full voltage range of the ADC and a common mode rejection ratio of about 100 dB.

Prior to collecting data, all system components are calibrated to establish, for example, the ultrasonic spatial and frequency responses, including hydrophonic responses; receiver bandwidths; the gain of the preamplifiers 18 and input noise level; any integral and differential non-linearities; any harmonic and IM distortion; any spurious-free dynamic range of the ADCs; and any background transients naturally-occurring within the measured frequency band. The amplitude and phase differential between channels may then be measured and compensated.

Figure 2:
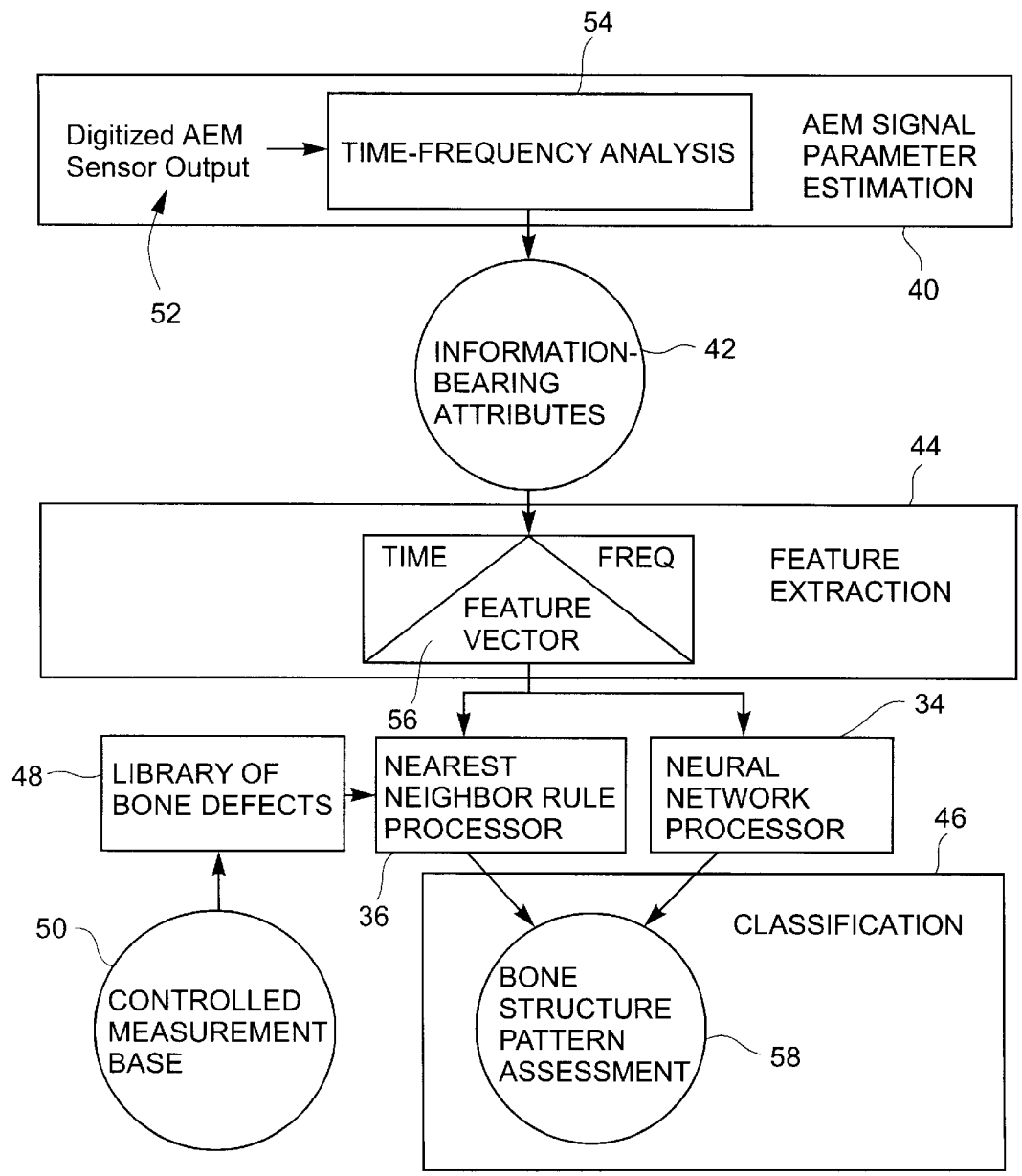
FIG. 2 is a flow diagram of data processing for determining bone condition.

For determining bone condition, the system 10 processes input data signals as AE signals from the transducers 12 according to the data flowchart in FIG. 2 by performing AEM signal parameter estimation in step 40 for determining information-bearing attributes 42; by performing feature extraction in step 44 from the attributes 42; and by classifying the extracted features in step 46 using a trained neural network 34 and/or an NNR processor 36, in which the NNR processor 36 processes the extracted features relative to a library of bone defects 48 generated from a controlled measurement base 50 obtained from in vivo and/or in vitro bone condition measurements.

The system 10 performs AEM signal parameter estimation in step 40 by receiving digitized AEM sensor outputs 50 from the data acquisition and control logic card 24 to perform time-frequency analysis in step 54 using the DSP card 26 to generate the information-bearing attributes 42, such as the fine detail structure of the waveform and spectrum; the energy level in various frequency bands; the spectral correlation envelope; the rms bandwidth; the envelope decay; and the emission count rate.

The waveform of the received AE signals provides information regarding many unique aspects of the tissue microstructure and stress history of the source and the propagation path between source and sensor. In addition, the location and time of an AE are also important characteristics of the AE. Evaluation of the many parameters which describe single AE events provide a method to measure in vivo bone strength, and may extend to the point in which specific AE parameters may produce an acoustic structural fingerprint of different pathological processes within bone.

In a classical sense, the problem of defining the spatial distribution of AE sources and their temporal behavior is one of solving the inverse source problem, which infers knowing the dynamic Green's function of the structure and performing a series of deconvolution operations which are computationally intensive and noisy processes. The system 10 uses a more practical approach to this problem by using a neural network 34 as a neural network processing system which learns sets of various classes of structural failure from the measured AE signal and, after a sufficient period of time in this learning or training mode, operates to perform in an analysis or monitoring mode in which subsequent AE signals are processed for internal stress classification, in accordance with the previously learned data.

The system 10 is a wideband AEM system which uses wideband transducers 12 and high-speed DSP processors 26 to measure and quantify the significant information-bearing attributes of the AE of bone tissue. These distinct features, together with pattern comparison chips and/or neural networks, provide a diagnostic and classification instrument with a self-learning analysis capability for automatic screening and monitoring osteoporosis as well as other bone pathologies. In the system 10, the interfering transients from bone tissue, from the measuring AEM equipment, and from the environment are defined and minimized. The information-bearing attributes 42 in the wideband AE signature are determined and related to an architectural model of bone tissue. The information-bearing attributes 42 are used by the feature extraction step 44 from time-domain and frequency-domain processing to define a feature vector 56 to reduce the pattern vector (i.e. the measured AE waveform) to a vector of lower dimension which includes most of the useful information from the original vector. This information is dependent on the physical variables which characterize the source and the propagation path. The feature extraction in step 44 estimates a set of N features from the measured input waveform, each of which is a combination of all of the M measurements, N<M, and is considered to be a point in N-dimensional feature space.

Linear estimation theory indicates that the product of the simultaneous measurement of the rms time-delay error $\Delta t$ and rms frequency error $\Delta f$ is inversely proportional to the product of the rms bandwidth (W) and time duration (T) and the ratio of signal energy (E) to noise power per Hz ($N_0$), according to:

$$\Delta t \Delta f = \frac{1}{(WT)(2E/N_0)}$$

Biological AE signals are essentially transient in nature, which would imply a (WT) product close to unity. Thus, measurement accuracy in the time and frequency domains depend primarily upon the signal energy-to-noise power ratio. For a given AEM system, this ratio also establishes the rate C of receiving and processing sampled data (bits) is:

$$C = W \log_2 (1+P/N) = W \log_2 (1+(E/N_0)WT)$$

in which P=E/T is the average power and $N=N_0W$ is white thermal system noise. For a given time duration-bandwidth product or AE signal set, the data rate capacity and measurement accuracy of the system 10 increases with increasing signal-to-noise ratio, which is used in induced internal bone stress waves or AE signals for early diagnosis of osteoporosis in a clinical setting. A maximum ratio in data collection is preferable for both in vitro and in vivo testing.

The AE information-bearing attributes 42 include the fine detail structure of the waveform and spectrum; the energy level in various frequency bands; the spectral correlation envelope; the rms bandwidth; the envelope decay; and the emission count rate. These attributes 42 are intimately related to the class of incipient fault or defect in bone. Therefore, characterization of bone defects requires both time-domain and frequency-domain analysis. The last two attributes are derived from the time domain, while most of the signature attributes are derived from the frequency domain. Heretofore, only the emission count rate has been measured in previous experiments over the last 25 years.

The spectral line structure of the raw AE signature is defined with the utilization of a Discrete Fourier Transform (DFT) by the DSP card 26. The direct application of the DFT results in an efficient procedure for coarse frequency estimation. The procedure is efficient both from the standpoint of digital processing, in which the FFT may be utilized by the DSP card 26, and from the standpoint of achievable frequency estimation accuracy versus signal-to-noise ratio (SNR). Trends in the FFT spectrum are removed through median filtering, extraction of corrupting tonals, and removal of spectral "hash" by thresholding.

A non-linear coherence function, typically used in characterizing component wear in vibrating machinery, measures the correlation between spectral components at different frequencies of the same event and of different events. The cross-correlation function between transducers 12 is computed as a localization measure of acoustic emission sources in the correlation processor 41.

The set of space-time cross-correlation functions will permit the corresponding times-of-arrival for the various sensors to be estimated. The resulting set of times-of-arrival, together with a priori knowledge of the exact location of the array sensors, an anatomical model of the biological structure being monitored, and stored in vivo estimates of the velocity of sound for the various tissues, will permit the AE source locations to be uniquely determined. Spatial localization of the AE events is important in eliminating noise and artifacts and may facilitate the identification of various pathologic conditions.

The masking interfering transient bursts recorded in the in vitro experiments, due to the environment and measuring instrumentation, are characterized and minimized to achieve an acceptable signal false alarm rate and to maximize the signal-to-noise ratio for parameter estimation accuracy. Signal processing will examine the information attributes of the recorded waveforms on the various channels and use them to establish the signal set produced by a common AE event. The AE information bandwidth is maximized with Fourier processing and correlation of the processed acoustic emissions to the properties of bone tissue that relate to tissue strength.

Recognizing that the AE spectral signature includes structural information, spectrum analysis provides reliable estimates of characterizing parameters, such as spectral level (or power) and bandwidth.

A spectral moment estimation (SME) technique is used to estimate various moments of the bandlimited demodulated AE signal power spectrum. SME has been successfully employed to analyze the ionization wake signature associated with reentry vehicles and to detect and identify underwater acoustic transients. It is anticipated that the SME is more sensitive to the dynamics of spectral structure than other signal processing techniques, due to the moment estimators depending on the rate of change and "curvature" of the radiated power spectrum.

The first three spectral moment estimates of the signal; i.e. the power, power mean frequency, and mean-square bandwidth, are defined in terms of an estimate of the desired AE power spectrum. The biases and variances of the spectral moments are independent of the actual mean frequency, and are functions of the record length, spectrum width, and spectrum shape and approach zero as the record length increases or as the bandwidth decreases. Unbiased estimates also occur when the power spectrum is symmetrical about its mean. However, the expected value of the power estimate is generally unbiased and yields, on the average, the total received power in the process. It is also possible to estimate the spectral moments in the time domain without computing an FFT, which saves considerable computing time and is evaluated in the program.

Referring to FIG. 2, the information-bearing attributes 42 of the acoustic signature identified above may be used as components of a feature vector 56 for pattern recognition. Additional input parameters to the classifier may also include specific patient information such as gender, age, height, weight, and medical record. The feature vector is derived in the feature extractor 40 and in the preferred embodiment, is used to drive the neural network 34 and/or the NNR processor 36 to generate a bone structure pattern assessment 58 corresponding to the bone tissue under test. The neural network 34 s thus adapted to track and predict bone fatigue.

In an alternative embodiment of the invention, the classifier may be based upon other statistical approaches to pattern recognition, such as hypothesis testing and multivariate regression analysis.

Using AEM technology, an accurate and reliable measure is provided to indicate the automatic indication of imminent bone degradation. For in vivo monitoring and data acquisition, the recording of AE signals from bone tissue in a database in the hard drive 28 is naturally corrupted by system and body noise and artifacts. Because of the richness of the parameters to be evaluated by the system 10, specific pathological AE characteristics are identified above and beyond the strength estimation. The system 10 may be used, for example, on postmenopausal osteoporosis, but may be applied as well to identify characteristic AE profiles associated with varying degrees of osteoporosis, as opposed to normal bone in patients with low BMD who have not fractured compared with bones which have fractured, and with characteristics associated with cancellous versus cortical fractures. Because the acoustic emissions are a function of material, different crystallization, different crystal to matrix ratio, and different types of resorption and periosteal acquisition, the system 10 and method offers important information which is not currently available with existing technologies.

The ultrasound properties of bone, together with morphological studies, are well known and extremely valuable in establishing functional relationships and assessing pathologies. The mechanical properties of bone, such as its strength and toughness and its structural adaptation depends on its architecture at the microscopic and macroscopic level. Because it is an anisotropic material, bone tissue has relatively complex failure modes.

Signal characteristics as a function of various loads allow bone strength to be estimated more accurately than by BMD determination, and also more accurately than conventional AE technology.

The neural network 34 is used as a classifier to predict the start of bone fatigue, utilizing the derived information-bearing attributes of the AEM signature as the input excitation. Using the system 10, AE signals emitted from bone tissue due to applied stress are detected, and a correlation of parameters characterizing AE signals with bone strength is determined. The data acquisition of AE signals through the soft tissue envelope of normal human anatomy is also performed. The classification of AE signals from the human anatomy is then performed by the neural network 34, and appropriate loading methods for human bones, such as the forearm, are developed to induce detectable and classifiable AE signals.

Measurable altered wideband AE profiles in patients with decreased bone strength may then be determined, and a correlation of the AE profile with bone architecture and bone pathologies is determined.

The classification processing of input data is shown in the flow diagram in FIG. 2. The basic problem of bone classification is to assign each possible measured AE signature vector or point in N-dimensional feature space to a suitable bone structural defect pattern class. A robust statistical decision rule for pattern recognition which gives very good results for a sparse observation data base, and may thus prove well suited for discriminating bone defect data recorded in a clinical setting, is the NNR. The NNR assigns a given defect class to the unknown AE signature data set if its feature vector is closest to the measured feature vector, according to a predetermined closeness criteria.

NNR processing is a non-parametric classification procedure which exchanges the need to know the underlying probability distributions of the data set for that of knowing the distinct feature vectors of the desired defect patterns. It is a minimum distance classifier in that it indicates an unknown defect is of a specific bone defect type when its feature vector is closest to the mean feature vector of a cluster of feature points included in a library, derived from known bone diseases and accompanying bone defects. In the large sample case, the NNR processor 36 produces a probability of error bounded above by twice the Bayes error and below by the Bayes error.

The system 10 selects the feature vector for the bone defect that has minimum dimensionality and also produces maximum separation between defect classes to minimize class overlap due to noise and measurement error. For each class of source events being analyzed, the mean and variance of each feature is calculated. The choice of storing the variances of the individual feature attributes rather than the full covariance matrix of the feature set enhances the computational and storage efficiency. Based upon the computed means and variances, distance measures are defined for each bone defect class which gives the distance of any defect event from that class. It is expected that the variances are more effective in distinguishing the differences between tightly clustered classes and widely spread ones. For a source event j from a bone defect class i, the distance $D_{ij}$ is given by $$D_{ij}^2 = \sum_k \frac{(x_{jk} - u_{ik})^2}{v_{ik}}$$

in which $u_{ik}$ is the mean of the $k^{TH}$ feature of the $i_{TH}$ bone defect class, $v_{ik}$ is the corresponding variance, and $x_{jk}$ is the value of the $k^{TH}$ feature of event j. From this, measure, the probabilities of the various structural bone defects are estimated. In practice, a successful NNR technique includes a safeguard against "forced" classification or excessive misclassification error by resorting to a rejection test, based on a majority acceptance level.

The probability distribution of the sample variances of the feature attributes is represented by the well-known chi-square distribution, which uses a sample size of about 200 time samples required to estimate the sample standard deviation to within 10% of the true value, with a 95% confidence level. Statistical testing to assure the set of time samples is of sufficient size to provide clinically meaningful confidence levels.

The system 10 includes a neural network 34 for determining the fatigue life of the bone tissue, depending on the measured variances of the AE parameter attributes. When the correlation between acoustic emissions, such as from different transducers 12, and bone stress have been determined and found compatible with convergence requirements in neural network design, the self-learning neural network 34 is used for analyzing and classifying the AE signature of bone tissue.

The input to the neural network 34 is the information-bearing attributes 42 of the AE signature, its processed Fourier spectrum, or a feature vector 56 containing the attributes as components. The output is a measure of the stress differential history associated with given metabolic bone failure events.

The neural network 34 includes a set of processing nodes, biologically termed "neurons", and weighted paths connecting these nodes. The basic type of neural network considered appropriate for AE classification is a 3 or 4 layer feed-forward network with supervised training, using the back-propagation rule. Input data enters the neural network 34 at the input layer, and the processed information is retrieved at the output layer, with one or two hidden layers existing between the input and output layers. The output of the current $i^{TH}$ node is obtained by calculating the activation level, $E_i$, according to:

$$E_i = \left(\sum_j w_{ij} p_j\right) + b_i$$

in which $w_{ij}$ is the connection weight from the previous layer's $j^{TH}$ node to the current $i^{TH}$ node, $p_j$ is the output or activation of the $j^{TH}$ node, and $b_i$ is the bias of the $i^{TH}$ node.

In one embodiment, the activation function of a neuron is an exponential type of input/output (I/O) response, according to:

$$Output = p_i = \frac{1}{1 + e^{-Input}}$$

in which the input INPUT=$E_i$, the sum of the weighted outputs of all the connected neurons and a threshold term. The output vector is the classification of the input vector corresponding to a function of the input pattern as transformed by the network weight matrices.

For using a neural network, the matrix of connecting weights is to be determined. This is the "learning" mode which utilizes the input training patterns and the output training pattern to store the patterns to be recognized in the network connections. When an unknown input AE pattern is presented, the neural network 34 determines to which class the pattern belongs by modifying the weighting elements in a direction that maximally lowers the output error (the gradient descent approach), and minimizing the error between the sum of squared differences between the output layer nodes and the desired outputs. After training, the neural network 34 is operated in a monitoring mode to identify the start of serious bone degradation based on the training.

The proper selection of training data to achieve acceptable classification accuracy involves the number of training samples needed and the information and variability included in the training samples selected from distinct AE patterns. The training sets are derived from the AE signatures for tissue with varying weight loss and loads, with compression and bending, and recorded at several sensor sites. The training samples may be obtained from in vitro human bone tissue measurements and/or in vivo bone samples. Neural network training is significantly enhanced by incorporating some a priori knowledge of the architectural model of bone tissue in the neural network architecture.

Some of the difficulties in selecting the training data are (1) signal dynamics due to geometry and anisotropicity, (2) variable non-random noise due to inhomogeneities, and (3) the amount of time necessary for training. For example, a three layer neural network with a number I of input nodes, one hidden layer with H nodes, and a number O of output nodes, the total processing time $T_p$ for training the neural network 34 is:

$$T_p = (I \cdot H + H \cdot O) N_p N_t U_t$$

in which $N_p$ denotes the number of training AE patterns, $N_t$ denotes the average number of iterations required for training a specific AE pattern, and $U_t$ is the unit time taken for executing one iteration. The training data set may be selected, in part, to minimize the processing time.

The trained neural network 34 provides a real-time fatigue life estimator of bone tissue. During normal activity, bone continually accumulates fatigue damage, such as stress fracture. The fatigue strength of bone tissue is determined by subjecting bone to a cyclic stress and determining the number of cycles to induce failure. The training data set for estimating bone fatigue is generated based primarily on uniaxial testing, with input from rotation, bending and flextural testing. The uniaxial local strain model has the following relationship between the total strain range $\Delta L$ to the total stress range $\Delta T$:

$$\Delta L = \Delta T / E + \Delta L_p$$

in which E is the elastic modulus and $\Delta L_p$ is the plastic strain range. The latter term is the non-linearity that modifies Hooke's law and results in the occurrence of hysteresis loops in the stress-strain (T-L) plane. These hysteresis loops characterize the degree of fatigue damage caused by the corresponding component load variations. The fatigue damage of a load cycle may be defined by the number of times such a cycle may be repeatedly applied before a crack develops in bone tissue, and produces an acoustic emission. It has been shown that for both cortical and cancellous bone, the compressive strength $F_c$ may be expressed as $$F_c = K \dot{L}^A \rho^B$$

in which $\dot{L}$ is the strain rate, $\rho$ is the bone density, the constant A is about 0.06, the constant B is about 2 and 0, for cancellous and cortical bone, respectively, and K is a constant of proportionality, depending on the reference values for strain rate and density. These equations are used to define neural network computation, and depend on the data acquisition of load cycles. Once trained, the neural network 34 provides an accurate classification of the bone condition within a predetermined error tolerance.

It is envisioned that as an extension of the preferred embodiment, fuzzy logic can be incorporated into the neural network 34 to speed up convergence and into the NNR processor 36 to refine the set of distance measures. In the neural network case, the actual weights will be fuzzy numbers and the thresholding of the neuron will be a fuzzy set. In the NNR case, the set of distance measures will be a fuzzy rule base that is defect class dependent.

In use, the system 10 and method uses the AE signature as a true wideband process, as it naturally occurs during the physical generation process. The system 10 and method operate with spatial precision, such that events in the region-of-interest (ROI) may be isolated, and so that other fine detail parameters of the AE signature may be measured and tracked. Spatial precision is an important method of noise elimination and determination of the ROI where the AE events are occurring. Precise localization of the signal within bone tissue is important for identifying various pathologic conditions.

Figure 3:
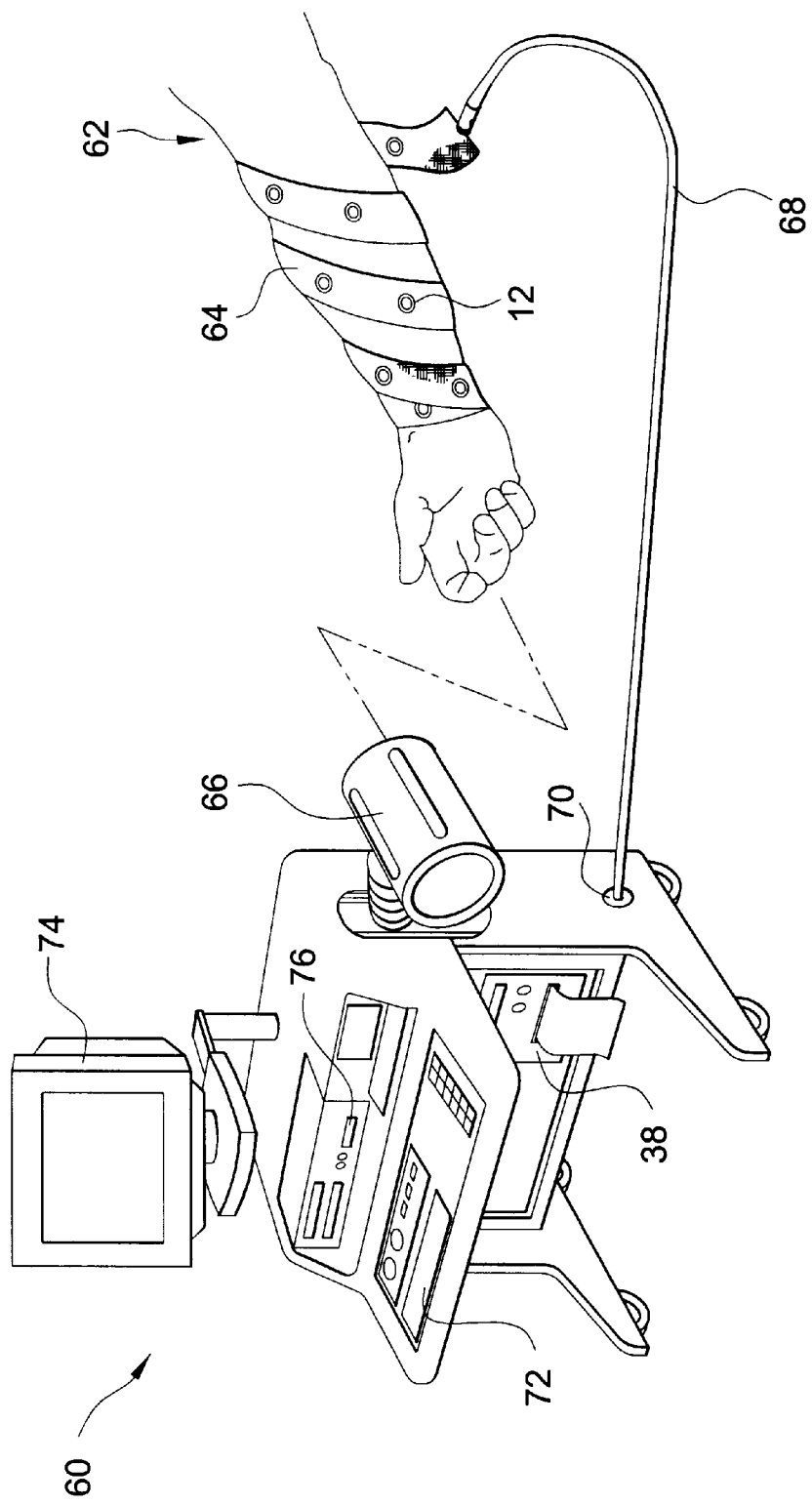
FIG. 3 illustrates a stand-alone terminal implementing the present invention.

The system 10 is adapted to perform both axial compression and testing of, for example, the mid-shaft in a four point bend of the human forearm. The range of compression load is from about 0 to about 100 pounds. As shown in FIG. 3, the system 10 may be a stand-alone terminal 60, and the forearm 62 may be placed substantially adjacent a plurality of transducers 12 disposed on a wrap-around strip 64, such that the transducers 12 may receive AE signals when predetermined loads are applied to the forearm 60 by cuff 66 when the forearm 62 with strip 64 is positioned within the cuff 66. A connection 68 is provided for operatively connecting and providing input data signals from the transducers 12 to an input port 70 of the terminal 60. The forearm may be evaluated since it is a common site of osteoporotic fractures, and the anatomy of the forearm allows easier application of loads and sensors, as compared to the spine or hip.

The system 10 may include a printer 38 as well as other input and output devices such as a keyboard 72 and a display 74, with the keyboard 72 for receiving operating commands, and the display 74 for visually outputting the results of the classification of the bone condition of the forearm 62.

In one embodiment, the system 10 may be the stand-alone terminal 60 as in FIG. 3 which includes the components shown in FIGS. 1–2, including the neural network 34, the NNR processor 36, and the library of bone defects 48 using the controlled measurement base 50. Such components may be implemented in hardware and/or software; for example, the library of bone defects 48 and the configuration of the neural network processor 34; i.e. the weights and biases of the neurons, may be transferred to the system 10 using a portable medium such as a computer disk, which the system 10 may then read using a disk drive 76.

Figure 4:
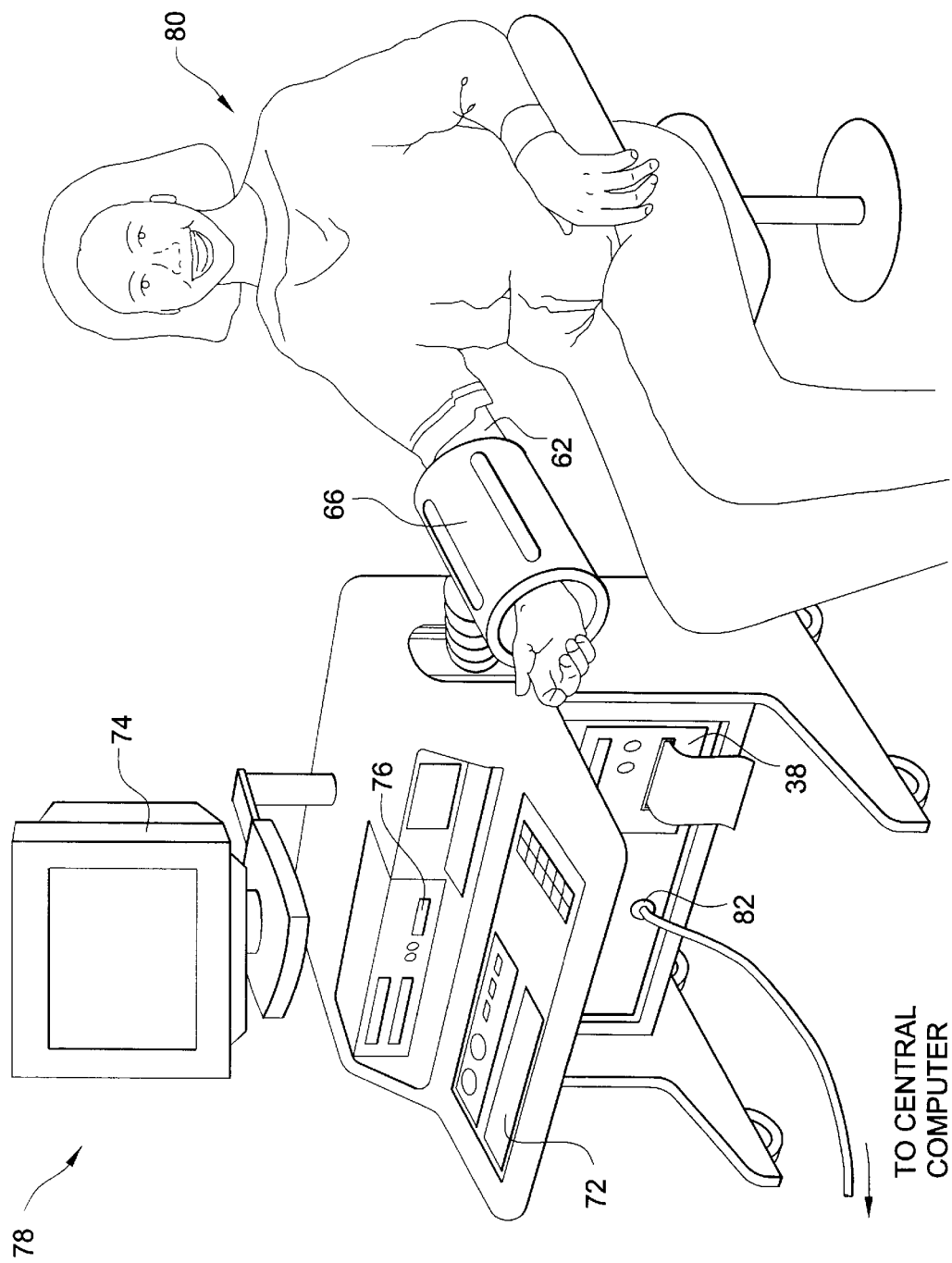
FIG. 4 illustrates a remote terminal implementing the present invention.

Alternatively, as shown in FIG. 4, the system 10 may be configured to include at least one remote terminal 78 which has the transducers 12 disposed in the cuff 66 and substantially adjacent the forearm 62 of a patient 80. The remote terminal 78 is operatively connected to a central computer (not shown in FIG. 4) through an I/O port 82, which may be a telephone jack for connecting the remote terminal 78 to the central computer via a modem, which may be internal or external to the remote terminal 78.

The central computer may centralize the processing power and components of the system 10, such as the pre-amplifiers 18, the filters 20, the CPU 22, the cards 24–28, the bus 32, as well as the neural network 34, the NNR processor 36, the library of bone defects 48 and the controlled measurement base 50, to be shared among a plurality of remote terminals 78. Accordingly, the remote terminal 78 may be located in a regional osteoporosis clinic which remotely communicates AE signals from a patient 80 to the central computer, and the central computer then outputs the classification of the bone condition to the terminal 78 for output through the printer 38 or the display 74.

While the disclosed bone condition data acquisition system and method have been particularly shown and described with reference to the preferred embodiments, it is understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. A noninvasive bone condition data acquisition system for sensing, receiving, processing, detecting, localizing and classifying transient, wideband acoustic emission signals emitted by rapid structural changes in the human musculo-skeletal system due to externally applied mechanical loads, comprising:
   an array of wideband transducer sensors for measuring tissue surface vibrations in skin;
   a wideband recorder for receiving and recording induced acoustic emission signals from mechanically stressed bone tissue;
   processing means for deriving information-bearing attributes of the acoustic emission signals, extracting at least one set of one-way times of arrival from the sources of structural defects to said array of transducer sensors, deriving locations of structural defects from the at least one set of times of arrival and extracting a feature vector from the information bearing attributes; and
   a signal processor driven by the feature vector for classifying a bone feature selected from the group consisting of architectural integrity, fatigue strength and bone quality.

2. A noninvasive bone condition data acquisition system as in claim 1, wherein the recorder is configured to receive and record wideband acoustic emission signals.

3. A noninvasive bone condition data acquisition system as in claim 1, wherein the signal processor is a neural network for classification.

4. A noninvasive bone condition data acquisition system as in claim 1, wherein the signal processor is a nearest neighbor rule processor for classification.

5. A noninvasive bone condition data acquisition system as in claim 3, wherein the signal processor is a space-time cross-correlator for localization.

6. A noninvasive bone condition data acquisition system as in claim 1, further comprising database memory means containing a set of acoustic emission profiles for known patients, said database connected to said signal processor for establishing a comparative basis for classifying bone quality.

7. A noninvasive bone condition data acquisition system as in claim 6, wherein the set of acoustic emission profiles are based on patients exhibiting metabolic bone disease.

8. A noninvasive bone condition data acquisition system as in claim 7, wherein the acoustic emission profiles are based on known patients also having a history of osteoporotic fracture.

9. A noninvasive bone condition data acquisition system for sensing, receiving, processing, detecting, localizing and classifying transient, wideband acoustic emission signals emitted by rapid structural changes in the human musculo-skeletal system due to externally applied mechanical loads, comprising:
   at least one wideband transducer sensor for measuring tissue surface vibrations in skin;
   signal parameter estimator of at least one parameter from a digitized output of the wideband sensor to yield at least one information bearing attribute of the acoustic emission signal;
   feature extraction means for determining a feature vector from at least one information bearing attribute; and
   a signal processor for receiving said feature vector and comparing said feature vector to a library of known bone defects to yield a bone structure pattern assessment.

10. A noninvasive bone condition data acquisition system as in claim 9, wherein the signal processor is a neural network for classification.

11. A noninvasive bone condition data acquisition system as in claim 9, wherein the signal processor is a nearest neighbor rule processor for classification.

12. A noninvasive bone condition data acquisition system as in claim 9, wherein the signal processor is a Fourier Spectrum analyzer.

13. A noninvasive bone condition data acquisition system as in claim 9, wherein the library of bone defects is a database memory means containing acoustic emission profiles generated from testing on known patients.

14. A noninvasive bone condition data acquisition system as in claim 13, wherein the set of acoustic emission profiles are based on patients exhibiting metabolic bone disease.

15. A noninvasive bone condition data acquisition system as in claim 9, wherein said means for estimation comprises a digital signal processor.

16. A noninvasive bone condition data acquisition system as in claim 9, wherein said wideband sensor produces a receiving response of from about 30 kHz to about 3 MHz.

17. A noninvasive bone condition data acquisition system as in claim 9, wherein said wideband sensor comprises an array of sensors producing a receiving response of from about 30 kHz to about 3 MHz.

18. A noninvasive bone condition data acquisition system as in claim 17, wherein said sensors are simultaneously monitored to localize a given acoustic emission event and derive a source stress differential history associated with a given event.

19. A noninvasive bone condition data acquisition system as in claim 9, wherein said wideband sensor comprises a plurality of arrays of sensors producing a receiving response of from about 30 kHz to about 3 MHz.

20. A noninvasive bone condition data acquisition system as in claim 19, wherein the arrays of sensors are simultaneously monitored to localize a given acoustic emission event and derive a source stress differential history associated with a given event.

21. A noninvasive bone condition data acquisition system as in claim 16, wherein the wideband sensor produces a receiving response of from about 100 kHz to about 1 MHz.

22. A method for noninvasive bone condition data acquisition for sensing, receiving, processing, detecting, localizing and classifying transient, wideband acoustic emission signals emitted by rapid structural changes in the human musculo-skeletal system due to externally applied mechanical loads comprising the steps of:
   estimating at least one parameter of a digitized output of said wideband sensor to yield at least one information bearing attribute of the acoustic emission signal resulting from mechanically stressed bone;

extracting at least one feature vector with the at least one information bearing attribute as a component; and classifying the acoustic emission event using a signal processor by processing the at least one extracted feature relative to a library of such features recorded for various metabolic bone defects.

23. A method of noninvasive bone condition data acquisition as in claim 22, wherein said library of such features recorded for various metabolic bone defects is compiled by the step of generating a controlled measurement base obtained from bone condition measurements.

24. A method of noninvasive bone condition data acquisition as in claim 23, wherein the step of generating the controlled measurement base is obtained from in vivo bone condition measurements.

25. A method for noninvasive bone condition data acquisition as in claim 23, wherein the step of estimating a signal parameter to yield at least one information bearing attribute of the acoustic emission signal resulting from a mechanically stressed bone comprises the steps of:

receiving the acoustic emission with a wideband sensor and digitizing the sensor output; and performing time-frequency analysis on the digitized sensor output.

26. A method for noninvasive bone condition data acquisition as in claim 22, wherein the at least one estimated information bearing attribute is selected from the group consisting of detail structure of waveform and spectrum, energy level in multiple frequency bands, spectral correlation envelope, coherence between spectral components, rms bandwidth, envelope decay and emission count rate.

27. A method for noninvasive bone condition data acquisition as in claim 23, wherein the step of classifying the at least one extracted feature comprises the steps of:

utilizing the at least one information-bearing attribute as a component of a feature vector; and using the feature vector to drive the signal processor to generate measures for bone structure assessment.

28. A method for noninvasive bone condition data acquisition as in claim 27, wherein the signal processor is based on a neural network algorithm that generates a measure of the stress differential history permitting bone structure assessment.

29. A method for noninvasive bone condition data acquisition as in claim 27, wherein the signal processor is based on a nearest neighbor rule that generates distance measures from a library of measures metabolic bone failure events, permitting the bone structure assessment.

30. A method for noninvasive bone condition data acquisition for sensing, receiving, processing, detecting, localizing and classifying transient, wideband acoustic emission signals emitted by rapid structural changes in the human musculo-skeletal system due to externally applied mechanical loads, comprising the steps of:

estimating at least one signal parameter at multiple observation points utilizing an array of wideband sensors while maintaining a set of relative times-of-arrival of the respective acoustic emission signals to determine to yield at least one information bearing attribute of the acoustic emission signal resulting from mechanically stressed bone while also recording a set of relative times of arrival of the respective emissions signals at the sensors;

extracting a feature vector with at least one information bearing attribute as a component;

classifying the acoustic emission event using a signal processor by processing the extracted feature relative to a library of such features recorded for various metabolic bone defects; and localizing the acoustic emission sources by spatial and temporal correlation processing the set of relative times-of-arrival.

31. A method of noninvasive bone condition data acquisition as in claim 30, wherein said library of such features recorded for various metabolic bone defects is compiled by the step of generating a controlled measurement base obtained from bone condition measurements.

32. A method of noninvasive bone condition data acquisition as in claim 31, wherein the step of generating the controlled measurement base is obtained from in vivo bone condition measurements.

33. A method for noninvasive bone condition data acquisition as in claim 30, wherein the step of estimating a signal parameter to generate at least one information bearing attribute of the acoustic emission signal resulting from mechanically stressed bone comprises the steps of:

receiving the acoustic emission signal with wideband sensors and digitizing the sensor outputs; and performing time-frequency analysis on the digitized sensor outputs.

34. A method for noninvasive bone condition data acquisition as in claim 30, wherein the at least one estimated information bearing attribute is selected from the group consisting of detail structure of waveform and spectrum, energy level in multiple frequency bands, spectral correlation envelope, coherence between spectral components, rms bandwidth, envelope decay and emission count rate.

35. A method for noninvasive bone condition data acquisition as in claim 30, wherein the step of classifying the at least one extracted feature comprises the steps of:

utilizing the at least one information-bearing attribute as a component of a feature vector; and using the feature vector to drive the signal processor to generate measures for bone structure assessment.

36. A method for noninvasive bone condition data acquisition as in claim 35, wherein the signal processor is based on a nearest neighbor rule and generates the bone structure pattern assessment.

37. A method for noninvasive bone condition data acquisition as in claim 35 wherein the signal processor is based on a neural network algorithm driven by a set of acoustic emission signals, its processed Fourier spectra, or a feature vector containing the information-bearing attributes as components, that generate a measure of the stress differential history permitting bone structure assessment.

38. A method for noninvasive bone condition data acquisition as in claim 35, wherein the signal processor is based on a nearest neighbor rule driven by a feature vector containing the information-bearing attributes as components, that generates distance measures from a library of measured metabolic bone failure events, permitting bone structure assessment.

* * * * *